| United States Patent [19] | [11] Patent Number: 4,827,045 |
| Harandi et al. | [45] Date of Patent: May 2, 1989 |

[54] ETHERIFICATION OF EXTRACTED CRUDE METHANOL AND CONVERSION OF RAFFINATE

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 179,725

[22] Filed: Apr. 11, 1988

[51] Int. Cl.$^4$ .............................................. C07C 41/06
[52] U.S. Cl. ................................... 568/697; 568/699; 585/310; 585/318
[58] Field of Search ................ 568/697, 699; 585/310, 585/318

[56] References Cited

U.S. PATENT DOCUMENTS 4,090,949  5/1978  Owen et al.
4,709,113  11/1987  Harandi et al.

Primary Examiner—Howard T. Mars
Attorney, Agent, or Firm—Alexander J. McKillop; Charles J. Speciale; Charles J. Speciale

[57] ABSTRACT

An improved process for reacting crude aqueous methanol feedstock with iso-olefinic hydrocarbons to produce $C_5+$ methyl tertiary-alkly ethers, which comprises: contacting the aqueous methanol feedstock with a liquid hydrocarbon extractant rich in $C_4+$ iso-alkene under liquid extraction conditons; recovering an organic extract phase comprising the hydrocarbon extractant and a major amount of methanol introduced in the feedstock; reacting the extracted methanol and $C_4+$ isoalkene in contact with an acid etherification catalyst under catalytic reaction conditions to produce ether product; recovering an aqueous methanol raffinate phase containing the major amount of water introduced with the feedstock and a minor amount of feedstock methanol; and converting methanol from the aqueous raffinate phase to produce hydrocarbons.

4 Claims, 2 Drawing Sheets

ETHERIFICATION OF EXTRACTED CRUDE METHANOL AND CONVERSION OF RAFFINATE

BACKGROUND OF THE INVENTION

This invention relates to techniques for converting crude methanol or the like to lower methyl tertiary-alkyl ethers. In particular, this invention relates to an integrated system for converting crude methanol to valuable products by etherifying lower branched olefins, such as $C_4$-$C_7$ normally liquid iso-olefins. It is known that isobutylene and other isoalkenes produced by hydrocarbon cracking may be reacted with methanol over an acidic catalyst to provide methyl tertiary butyl ether (MTBE) and isoamylenes may be reacted with methanol over an acidic catalyst to produce tertiary-amyl methyl ether (TAME). Those ethers having the formula $CH_3$—O—R, where R is a tertiary alkyl radical, are particularly useful as octane improvers for liquid fuels, especially gasoline.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Increasing demand for high octane gasolines blended with lower aliphatic alkyl ethers as octane boosters and supplementary fuels has created a significant demand for isoalkylethers, especially the $C_5$ to $C_7$ methyl alkyl ethers, such as methyl tertiary butyl ether (MTBE) and tertiary amyl methyl ether (TAME). Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt%; however, the present invention is useful for removing water in lesser amounts or greater.

It is main object of the present invention to provide a novel and economic technique for removing excess water from crude methanol feedstocks, including novel operating methods and equipment for treating these oxygenate feedstocks prior to etherification and disposing of raffinate containing methanol. It has been discovered that aqueous methanol streams, such as etherification feedstock extraction byproduct can be economically upgraded by catalytic conversion concurrently with hydrocarbons.

SUMMARY OF THE INVENTION

A continuous technique has been found for converting crude methanol to methyl tertiary-alkyl ethers comprising methods and means for (a) contacting a crude methanol feedstock containing a minor amount of water with a liquid hydrocarbon extraction stream rich in $C_4$+ isoalkene hydrocarbons under extraction conditions favorable to selective extraction of the methanol, thereby providing an extract liquid stream rich in methanol and an aqueous raffinate stream lean in methanol;

(b) charging the liquid hydrocarbon and extracted methanol substantially free of water to a first catalytic reaction zone for contact with acid etherification catalyst under etherification process conditions for converting methanol to predominantly methyl isoalkyl ether;

(c) fractionating the etherification effluent from step (b) to unreacted recover methanol and light hydrocarbon overhead and $C_5$+ methyl tertiary-alkyl liquid product;

(d) catalytically cracking a heavy hydrocarbon stream and recovering liquid hydrocarbon cracking product, an olefinic liquid hydrocarbon stream containing $C_4$+ isoalkene; and a light gas stream; and (e) charging said aqueous raffinate stream from step (a) for conversion of methanol concurrently with cracking in step (d).

These and other objects and features of the invention will be understood from the following description and in the drawing.

DRAWING

FIG. 1 of the drawing is a schematic etherification process flowsheet depicting the present invention;

FIG. 2 is a flowsheet depicting relationships between verious unit operations and equipment configurations.

DETAILED DESCRIPTION

Figure 1:
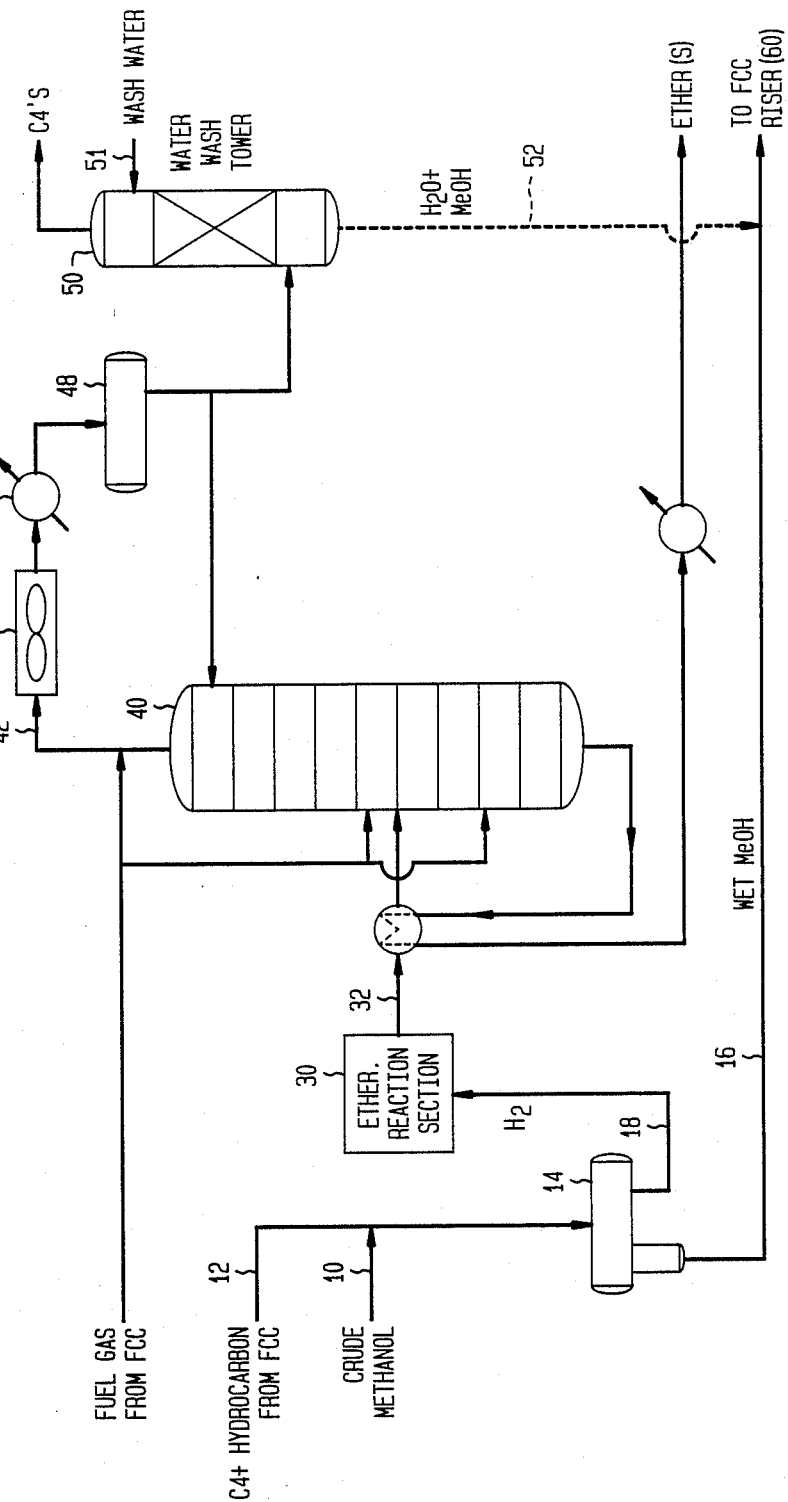

Typical feedstock materials for etherification reactions include olefinic streams, such as FCC light naphtha and butenes rich in isoolefins. These aliphatic streams are produced in petroleum refineries by catalytic cracking of gas oil or the like. The crude methanol commercially available from syngas processes may contain, for instance 4 to 17 wt% water, which must be removed, preferrably to a methanol purity of about 99.8 wt%. It has been found that more than 75% of crude feedstock methanol can be recovered by liquid extraction with light olefinic liquid extractant, such as butenes and $C_5$+ light olefinic naphtha. The typical feed ratio range is about 5 to 20 parts hydrocarbon extractant per part by volume of methanol.

Typical equipment according to the present invention includes a continuous feedstock separation and etherification reactor system for converting crude methanol oxygenate feedstock and isoolefin to methyl t-alkyl ether, wherein the unit operation apparatus includes: extractor means for contacting crude feedstock liquid containing a minor amount of water with a liquid hydrocarbon extraction stream under extraction conditions favorable to selective extraction of methanol, thereby providing an extract liquid stream rich in methanol and an aqueous raffinate stream lean in methanol; first catalytic reactor means operatively connected for contacting the extract stream in a catalytic reaction zone with acid etherification catalyst in an etherification reaction zone under process conditions to convert a major portion of methanol to ether; second catalytic reactor means for contacting said raffinate stream with methanol conversion catalyst in the presence of hydrocarbon to produce a liquid hydrocarbon stream; and means for charging at least a portion of said liquid hydrocarbon stream from said second reactor means to said extractor means as said extraction stream.

Referring to the drawing, a continuous stream of crude methanol (MeOH) feedstock is introduced via conduit 10 with a stream of $C_4$+ olefinic hydrocarbon liquid extractant introduced via conduit 12 to a top inlet of extraction separation unit 14, operated at about 35°-40° C. These streams are contacted under liquid extraction conditions to provide an aqueous raffinate phase. An aqueous stream containing a major amount of the water present in the crude feedstock is withdrawn via conduit 16. The lighter organic extract phase containing hydrocarbon extraction solvent and the major amount of feedstock methanol is recovered from extraction unit 12 via conduit 18, and introduced under temperature and process conditions suitable for conversion of methanol in contact with etherification catalyst in reactor system 30. From reactor 30, the effluent product stream passes via line 32 to a debutanizer fractionation tower 40. Tower overhead comprising unreacted $C_{4}+$ hydrocarbons and methanol are passed via conduit 42 and condenser means 44, 46 to liquid accumulator.

The debutanizer overhead product is sent to effluent washer vessel 50, where it is contacted with wash water introduced via line 51 for extraction of unreacted methanol from the unreacted light hydrocarbons.

The aqueous raffinate stream 16 consists essentially of water, partitioned methanol (50-80 wt%) and a trace of hydrocarbon. This stream is reactive at elevated temperature in the presence of an acid zeolite catalyst, such as type REY, ZSM-5, etc., in a fluidized reaction zone 60. For example, the aqueous methanol stream may be coreacted with olefins and/or heavy hydrocarbon feedstock in a conventional FCC riser reaction section, as described by Owen et al in U.S. Pat. Nos. 4,012,455 and 4,090,949, incorporated herein by reference. Preferrably, ZSM-5 is added to FCC catalyst to improve cracked gasoline octane. These acid medium pore zeolites also selectively onvert methanol to gasoline range hydrocarbons in the FCC reactor. The aqueous methanol may be introduced directly to the FCC riser zone (bottom or middle secton) or mixed with FCC hydrocarbon feed. Optionally, methanol-containing wash water from unit 50 may be converted along with the raffinate stream.

EXTRACTION UNIT OPERATION

The typical preferred crude feedstock material is methanol containing about 4 to 17% by weight water. The extraction contact unit may be a stirred multi-stage vertical extraction column adapted for continuous operation at elevated pressure. Any suitable extraction equipment may be employed, including cocurrent, cross-current or single contactors, wherein the liquid methanol feedstock is intimately contacted with a substantially immiscible liquid hydrocarbon solvent, which may be a mixture of $C_{4}+$ aliphatic components including lower alkanes, n-alkenes or relatively pure isoalkenes, such as isobutylene, etc. This unit operation is described in *Kirk-Othmer Encyclopedia of Chemical Technology* (Third Ed.), 1980, pp. 672-721. Other equipment for extraction is disclosed in U.S. Pat. Nos. 4,349,415 (DeFilipi et al), 4,626,415 (Tabak), and 4,665,237 (Arakawa et al). Unit operation details are also disclosed by Harandi et al in copending U.S. patent application Ser. No. 043,729, filed Apr. 29, 1987, incorporated herein by reference. The methanol extraction step can be performed advantageously in a countercurrent multistage design, such as a simple packed column, rotating disk column, agitated column with baffles or mesh, or a series of single stage mixers and settlers.

As an example of typical methanol extraction with FCC light naphtha in a liquid-liquid contact and separation unit for extracting crude methanol containing 4 wt% water at about 38° C. (100 F.). The extractor unit and water wash unit are operated at about 35°-65° C. (100°-150° F.) and 0-2000 kPa. The stream composition for each feed, light extract phase and heavy raffinate phase is given in Table I.

TABLE 1

| | Extaction Operation | | | |
|---|---|---|---|---|
| Component | FCC Light Naphtha | Crude Methanol | Light Liquid Phase | Raffinate Heavy Liquid Phase |
| Methanol (lbmol/hr) | 149.87 | 113.96 | 35.91 | |
| Water | | 11.11 | 0.40 | 10.71 |
| $C_4$ | 51.13 | | 50.98 | 0.15 |
| $C_5$ | 330.10 | | 329.23 | 0.87 |
| $C_6$ | 163.38 | | 163.02 | 0.36 |
| Total | 544.61 | 160.98 | 657.59 | 48.00 |
| Methanol Recovered (wt %) | | | 76.0 | |
| Water Entrained in Methanol | | | 0.2* | |

(*based on dry hydrocarbon feed)

ETHERIFICATION OPERATION

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, Dec. 1977. An article entitled "MTBE and TAME-A Good Octane Boosting Combo", by J. D. Chase, et al., *The Oil and Gas Journal*, Apr. 9, 1979, pages 149-152, discusses the technology. A preferred catalyst is a trifunctional ion exchange resin which etherifies, hydrogenates and isomarizes the reactant streams. A typical acid catalyst is Amberlyst 15 sulfonic acid resin.

Processes for producing and recovering MTBE and other methyl isoalkyl ethers for $C_4$-$C_7$ isoolefins are known to those skilled in the art, such as disclosed in U.S. Pat. Nos. 4,544,776 (Osterburg at al) and 4,603,225 (Colaianne et al). Various suitable extraction and distillation techniques are known for recovering ether and hydrocarbon streams from etherication effluent.

Figure 2:
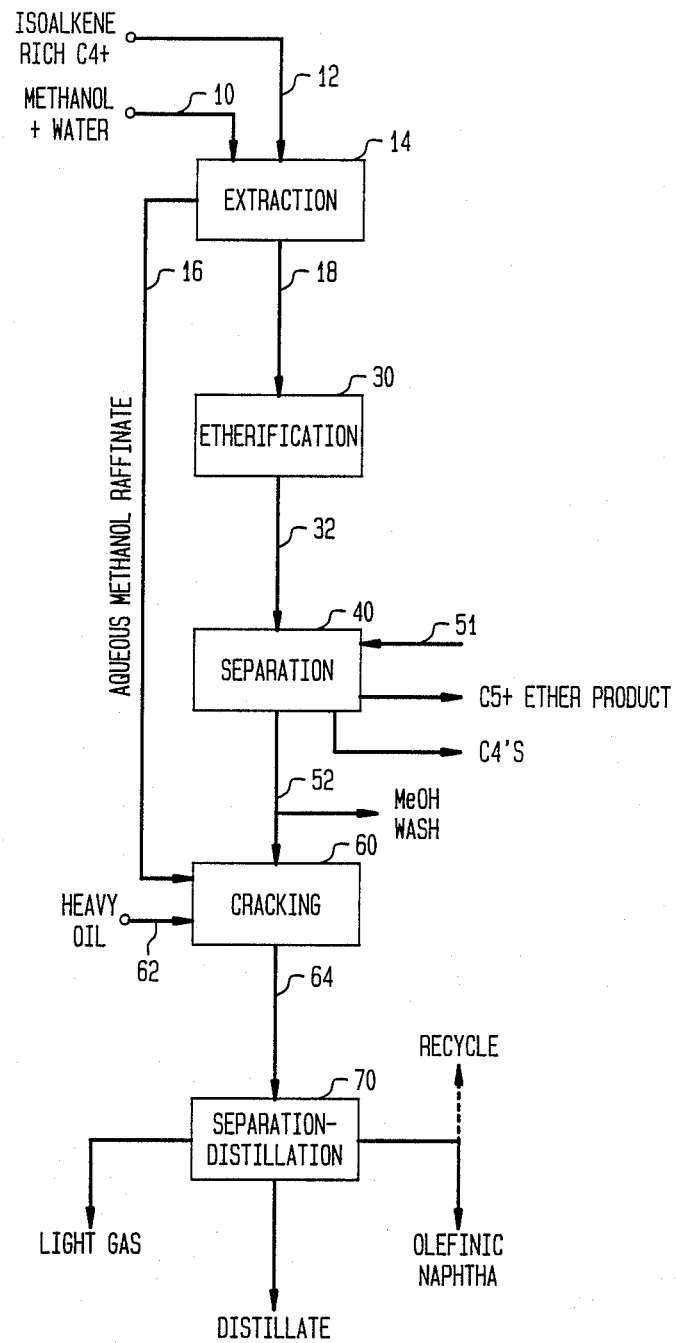

In FIG. 2, the various unit operations are depicted schematically to show the inter-relationships. A continuous feedstock separation and etherification reactor system is provided for converting crude methanol feedstock 10 to methyl t-alkyl ether. This system includes extractor means 14 for contacting crude feedstock liquid containing a minor amount of water with a liquid hydrocarbon extraction stream 12, which may comprise fresh isoalkene and/or a recycled $C_4$ olefinic mixture from FCC cracking. This unit operation is conducted under extraction conditions favorable to selective extraction of methanol, thereby providing an extract liquid stream 18 rich in methanol and an aqueous raffinate stream 16 lean in methanol. A first catalytic reactor means 30 is operatively connected for contacting the extract stream in a catalytic reaction zone with acid etherification catalyst in an etherification reaction zone under process conditions to convert a major portion of methanol to ether. Following separation of the etherification effluent in a distillation tower in unit 40 and optional washing of the tower overhead product to recover unreacted methanol, the raffinate 16 and wash stream 52 are passed to a second catalytic cracking reactor means 60 for contacting methanol from the raffinate stream with methanol conversion catalyst in the presence of hydrocarbon 62 to produce a hydrocarbon product stream 64. Following conventional separation and distillation of the cracking effluent, recycle means may be provided for charging at least a portion of the liquid hydrocarbon stream from the second reactor means to the extractor means as a reactive etherification feedstock and extraction stream. Optionally, FCC light gas may be passed to assist in etherification effluent separation by stripping volatile components from the ethers in unit 40.

The present invention is particularly advantageous in the economic dewatering of crude methanol, thus avoiding expensive and energy-intensive prefractionation by distillation. By extracting methanol from the crude feedstock with hydrocarbon reactant and converting the aqueous raffinate in the FCC riser reactor zone, substantial utility and equipment savings are realized.

Various modifications can be made to the system, especially in the choice of equipment and non-critical processing steps. While the invention has been described by specific examples, there is no intent to limit the inventive concept as set forth in the following claims.

We claim:

1. A continuous process for converting crude methanol to methyl tertiary-alkyl ethers comprising the steps of:
   (a) contacting a crude methanol feedstock containing a minor amount of water with a liquid hydrocarbon extraction stream rich in $C_4+$ iso-alkene hydrocarbons under extraction conditions favorable to selective extraction of the methanol, thereby providing an extract liquid stream rich in methanol and an aqueous raffinate stream lean in methanol;
   (b) charging the liquid hydrocarbon and extracted methanol substantially free of water to a first catalytic reaction zone for contact with acid etherification catalyst under etherification process conditions for converting methanol to predominantly methyl iso-alkyl ether;
   (c) fractionating the etherification effluent from step (b) to recover unreacted methanol and light hydrocarbon overhead and $C_5+$ methyl tertiary-alkyl ether liquid product;
   (d) catalytically cracking a heavy hydrocarbon stream and recovering liquid hydrocarbon cracking product, an olefinic liquid hydrocarbon stream containing $C_4+$ isoalkene; and a light gas stream; and
   (e) charging said aqueous raffinate stream from step (a) for conversion of methanol to hydrocarbons concurrently with cracking in step (d).

2. The process of claim 1 wherein the acid catalyst comprises ion exchange resin.

3. The process of claim 1 wherein the feedstock consists essentially of methanol and about 4 to 20 wt% water, and wherein the extraction liquid comprises a major amount of $C_4$-$C_5$ iso-alkenes.

4. The process of claim 3 including the step of passing at least a portion of said olefinic liquid hydrocarbon stream from step (d) to step (a) as liquid extractant.

* * * * *